United States Patent [19]
Houston et al.

[11] Patent Number: 5,894,014
[45] Date of Patent: Apr. 13, 1999

[54] STEAM DECONTAMINATION APPARATUS

[75] Inventors: John Christopher Houston, Erie;
Kenneth John Klobusnik, Lake City;
Susan Mary Napierkowski, Erie;
Francis John Zelina, Lake City; David James Zolner, Fairview, all of Pa.

[73] Assignee: Steris Corporation, Mentor, Ohio

[21] Appl. No.: 08/833,249

[22] Filed: Apr. 4, 1997

[51] Int. Cl.⁶ .................................................. A61L 2/06
[52] U.S. Cl. .................. 422/295; 422/105; 422/299; 49/360; 49/408
[58] Field of Search .................. 422/26, 105, 295, 422/299; 49/322, 449, 408, 404, 360

[56] References Cited

U.S. PATENT DOCUMENTS

| | | |
|---|---|---|
| 3,407,535 | 10/1968 | Purkey . |
| 3,488,142 | 1/1970 | Cooper .................. 422/295 X |
| 3,511,593 | 5/1970 | Thomas et al. .................. 422/295 |
| 3,694,962 | 10/1972 | McDonald et al. . |
| 3,717,434 | 2/1973 | Black .................. 422/295 X |
| 4,155,424 | 5/1979 | Johnson . |
| 4,228,135 | 10/1980 | Wolff .................. 422/296 |
| 4,670,227 | 6/1987 | Smith .................. 422/297 |
| 4,686,792 | 8/1987 | Terrian . |
| 5,225,160 | 7/1993 | Sanford et al. .................. 422/300 X |
| 5,237,777 | 8/1993 | Houston et al. .................. 49/360 |
| 5,238,660 | 8/1993 | Dietwart .................. 422/295 |
| 5,239,781 | 8/1993 | Napierkowski et al. . |
| 5,249,392 | 10/1993 | Houston et al. .................. 49/360 |
| 5,566,508 | 10/1996 | Houston .................. 49/445 |

*Primary Examiner*—E. Leigh McKane
*Attorney, Agent, or Firm*—Fay, Sharpe, Beall, Fagan, Minnich & McKee, LLP

[57] ABSTRACT

A steam sterilization device (10) including a chamber (12) having a slidable sealable door (30). A flexible insulating plastic member (74) covers the sealable door (30). The sterilization device (10) includes a frame (20, 22, 24, 28, 50) supporting the chamber (12). A front wall (60) of molded plastic covers the frame. A stop bracket (46) is secured to a door track (36) at the appropriate location below the door to limit travel. At least one counter weight (42) is secured to the door (30) by a cable (38) and a guide member (44) surrounds the counter weight.

18 Claims, 4 Drawing Sheets

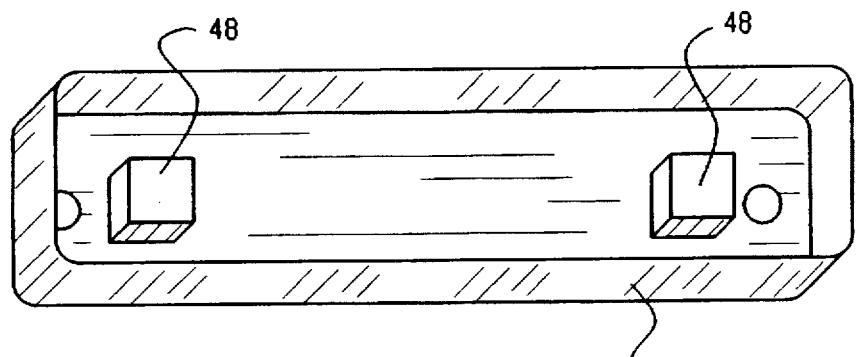
Fig. 4
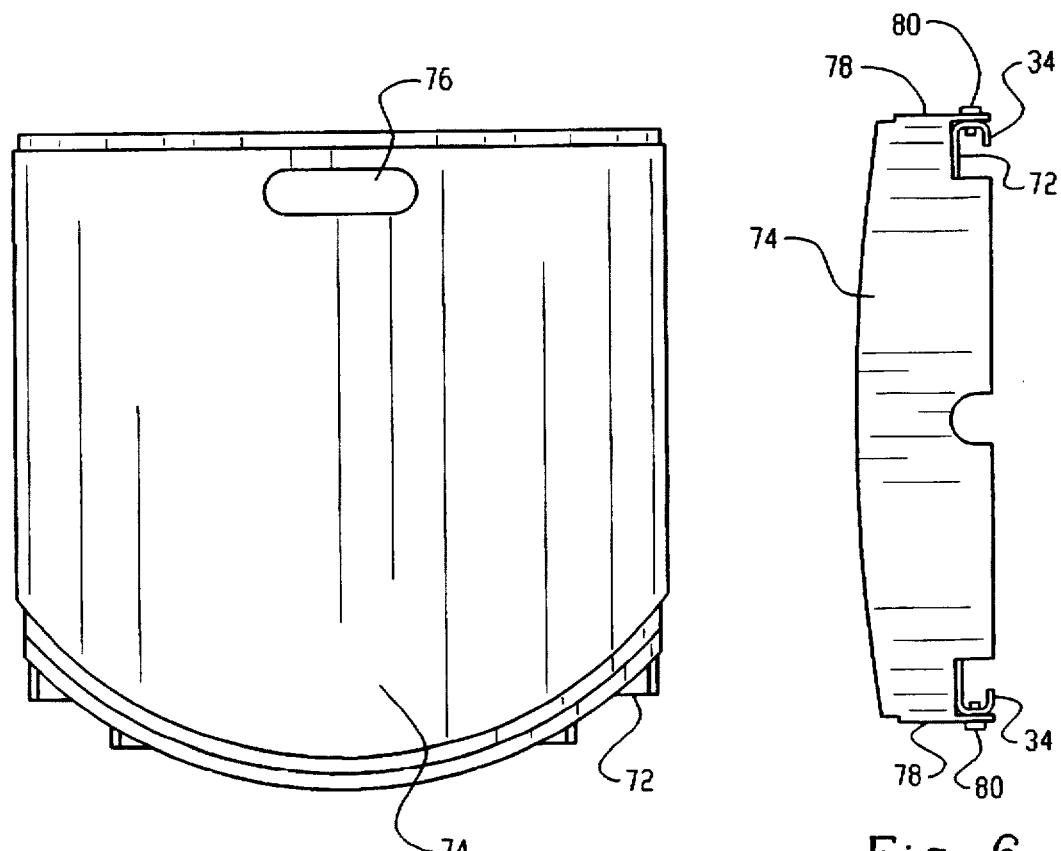
Fig. 5
Fig. 6

STEAM DECONTAMINATION APPARATUS

BACKGROUND OF THE INVENTION

The present invention relates generally to the decontamination art. It finds particular application in steam sterilization, disinfection and cleaning of medical, veterinary, mortuary and laboratory instruments and equipment and will be described with particular reference thereto.

More particularly, the present invention provides a mid-size sterilization device which does not require "house steam" and is operable on a standard power supply. In this regard, the present sterilization device is suited to small laboratories, emergency care facilities, as well as doctors and dentist offices. It will be appreciated, however, that the invention and its several embodiments may be applicable to a wide variety of environments in which the sterilization of instruments and equipment is required, including hospitals and other large institutions.

Medical, dental, surgical, veterinary and laboratory equipment and instruments are often sterilized by exposure to steam or steam in combination with other vapors. In this regard, an apparatus is provided which isolates the equipment and instruments in a high pressure, high temperature steam environment for a sufficient period of time to complete sterilization. For example, the steam autoclave devices of the type described in U.S. Pat. Nos. 4,193,818; 4,226,642; 4,601,300, herein incorporated by reference, provide examples of steam autoclaves of the type generally related to the present invention.

Historically, most steam sterilization devices have had special installation requirements such as a source of steam and a dedicated power supply, i.e. they did not connect to "appliance type" utilities. As more small and remote providers have developed in the medical industry, the demand for lower cost, easily installed steam sterilization devices has dramatically increased. Similarly, as third world countries develop greater requirements for sterilization equipment, lower cost stand alone units which nonetheless satisfies safety and regulatory requirements have become more necessary.

The present invention provides an inventive, sterilization device which provides the requisite, safety, installation flexibility and low cost.

SUMMARY OF THE INVENTION

In accordance with one aspect of the present invention, a steam sterilization device having a chamber for receiving articles to be decontaminated is provided. The chamber includes a slidable, sealable door which allows loading and unloading of articles from the chamber and a flexible insulation cover is secured to the door. The front of the sterilization device is covered by a molded plastic panel which is shaped to provide integral attachments for electronic components such as a microprocessor control panel. A frame supports the chamber, provides a mating surface for the plastic panel and supports a pair of opposed tracks for the door. A stop bracket is positioned horizontally below the door and between the tracks to act simultaneously as a stop member at the lowest point of travel for the door and as a catch basin for condensate. The door includes cable attachments to a pair of counter weights which are each housed in guide tubes. Each cable is run over a pulley arrangement formed integrally with the frame. Furthermore, a sensor is positioned on the frame to ensure the door is in a fully closed position prior to initiation of any sterilization cycles.

In a particularly preferred form of the invention, the counter weights are cylindrically shaped and the guide members are tubular. In an additional preferred form of the invention, the sensor is secured in a bore in the frame, the bore and sensor being sized such that the sensor must be threadedly or otherwise engaged at the lowest point in the bore to read a closed position for the door. In a further preferred form of the invention, the stop bracket is of a rectangular form having five walls with an open top.

Still further advantages of the present invention will become apparent to those of ordinary skill in the art upon reading and understanding the following detailed description of the invention.

BRIEF DESCRIPTION OF THE DRAWINGS

The invention may take form in various components and arrangements of components and in various steps and arrangements of steps. The drawings are only for purposes of illustrating a preferred embodiment and are not to be considered as limiting the invention.

FIG. 4 is a perspective view of the door stop of the inventive sterilization device;

FIG. 5 is a front elevation view of the chamber door of the inventive sterilization device;

FIG. 6 is a top view of the door of FIG. 5; and

DETAILED DESCRIPTION OF THE INVENTION

Figure 1:
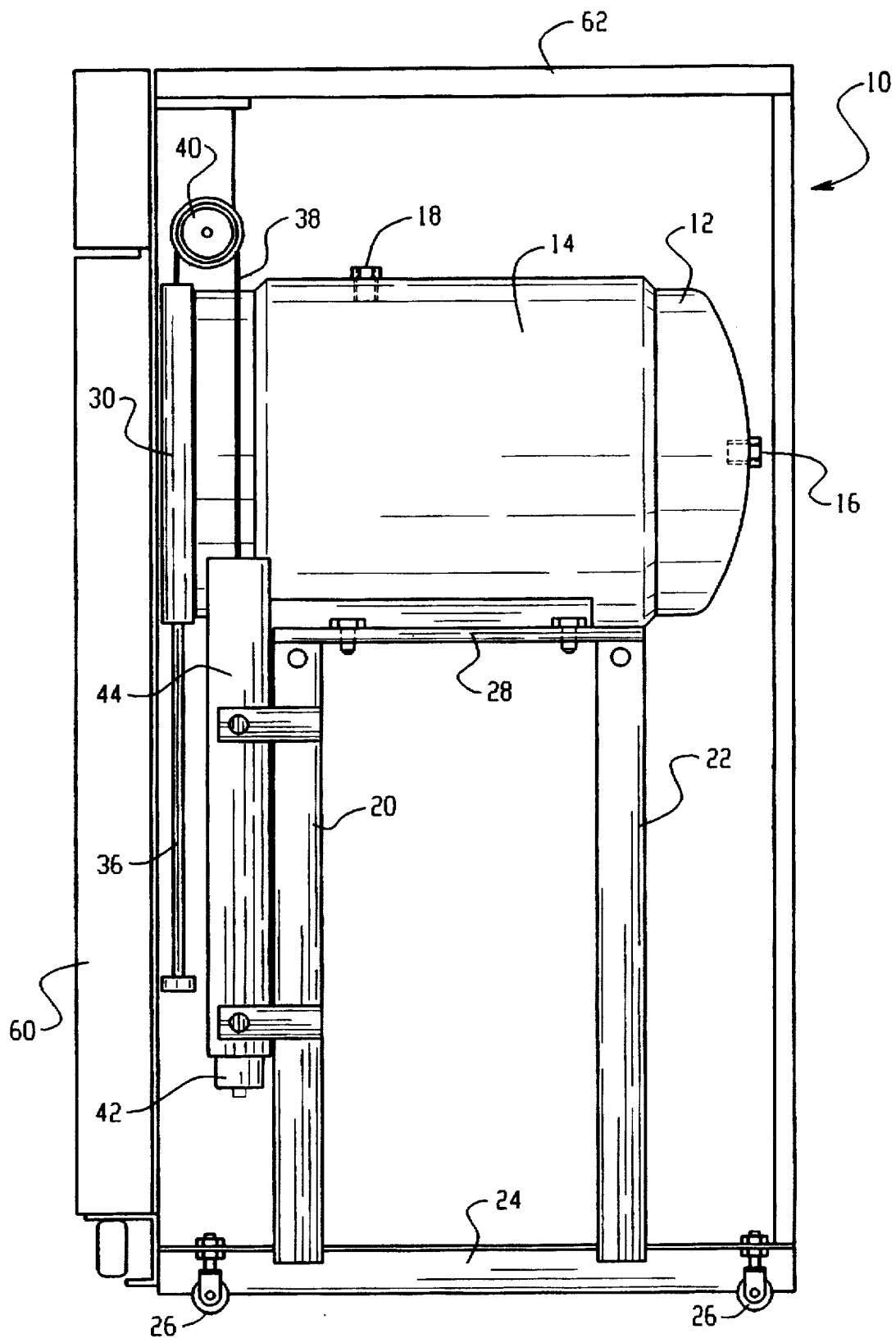
FIG. 1 is a side elevation view of the inventive sterilization device with a side panel removed.
Figure 2:
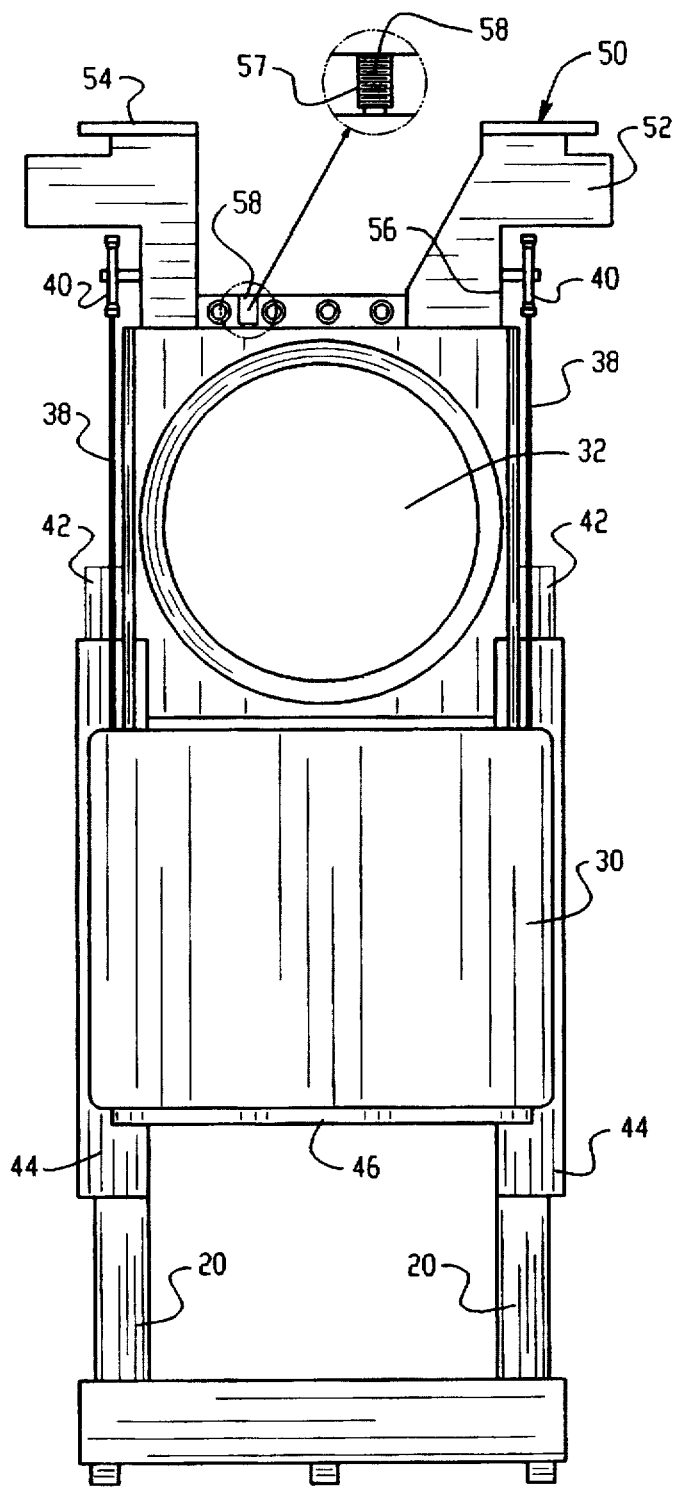
FIG. 2 is a front elevation view, with panels of the inventive sterilization device removed, and the chamber door in an open position.
Figure 3:
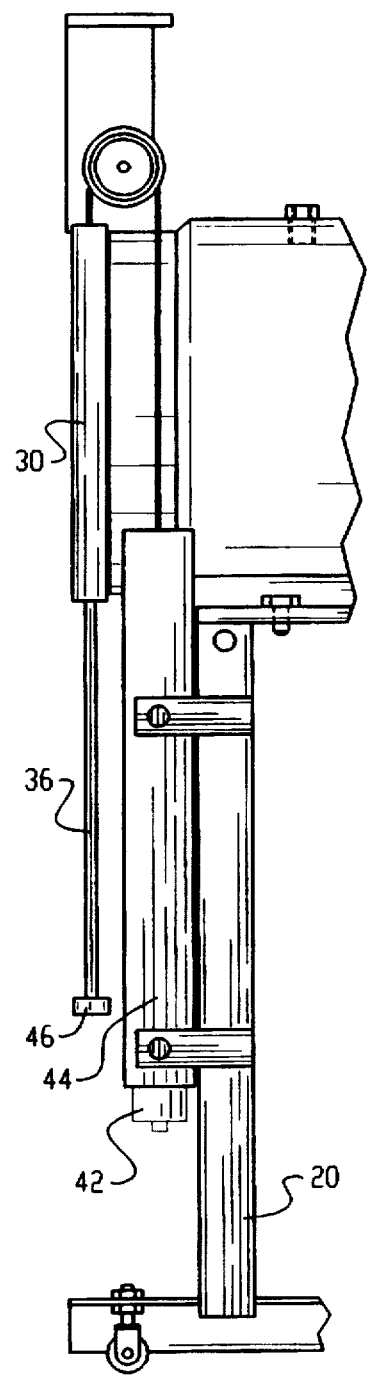
FIG. 3 is a side elevation view, of the inventive sterilization device of FIG. 2 having a closed chamber door.

Reference will now be made in detail to the present preferred embodiment of the invention, an example of which is illustrated in the accompanying drawings. While the invention will be described in conjunction with a preferred embodiment, it will be understood that it is not intended to limit the invention to that embodiment. On the contrary, it is intended to cover all alternatives, modifications and equivalents as may be included within the spirit and scope of the invention defined by the appended claims.

Referring now to FIGS. 1, 2, 3, and 6, in which like numbers are used to represent like elements, the inventive sterilization device 10 is depicted. The sterilization device 10 includes a sterilization chamber 12 surrounded by a jacket 14. Steam from a supply source (not shown) enters the chamber 12 through an inlet 16 and exits the jacket 14 through an outlet 18. The sterilization chamber 12 is supported by four vertical frame members, two front 20, and two rear 22 (wherein only those on one side of the device are depicted). The vertical frame members 20 and 22 are secured at a bottom end to a lower frame element 24 equipped with lockable and vertically adjustable casters 26 and to an upper frame element 28 which itself is secured to the chamber 12.

A door 30 is slidably positioned adjacent the front of chamber 12 and covers an opening 32. The door 30 includes side channel members 34 which mate with a pair of guide rods 36 and provide for vertical travel of the door 30. Preferably, the interactive portions between the door and the guide rods 36 are coated with a plastic such as, for example nylon, to facilitate a low friction interface. In its upper position, door 30 forms a seal with the opening 32 to the chamber 12 which allows pressurization and sterilization of articles in the chamber.

Travel of the door is controlled by a pulley system including a pair of cables 38 passing over a pair of pulleys 40 and secured to a pair of counter weights 42. A pair of hooks 43 interconnect the counter weights 42 with the cable 38. Counter weights 42 are themselves maintained within guide members 44 to provide lateral restraint and relatively quiet motion.

Travel of door 30 is also governed by a lower stop bracket 46 secured to the guide rods 36. As depicted, the stop bracket 46 is shaped as an open top receptacle that collects any condensate which may form adjacent the door of the sterilization device and which would otherwise drip on the floor adjacent the front of the unit and cause a safety hazard. In addition a pair of elastomeric members 48 are located in the stop bracket 46 to provide a cushioned end point of travel.

In the depicted invention, a particular advantage over prior design is provided by the cast aluminum upper frame member 50. A great cost savings is achieved with this member which simultaneously provides a front panel mounting surface 52, a top panel mounting surface 54, the pulley 40 mounting area 56 and a cast receptacle 57 for a door closed sensor 58. In this manner, a front panel 60, a top panel 62, and a side panel not shown, are easily securable to the device without individual fastening to an extensive framing network for the panels themselves. Moreover, the upper frame member 50 precisely positions the door counter balance assembly, provides precise mounting for the front panel, provides a precise placement for the top panel and provides attachment for the door up sensor. Particularly, only when sensor 58 is fully threaded into bore 57 is it located close enough to the door to read a closed position. In this manner, the sensor cannot be improperly positioned and yet allow the sterilizer to operate.

Figure 7:
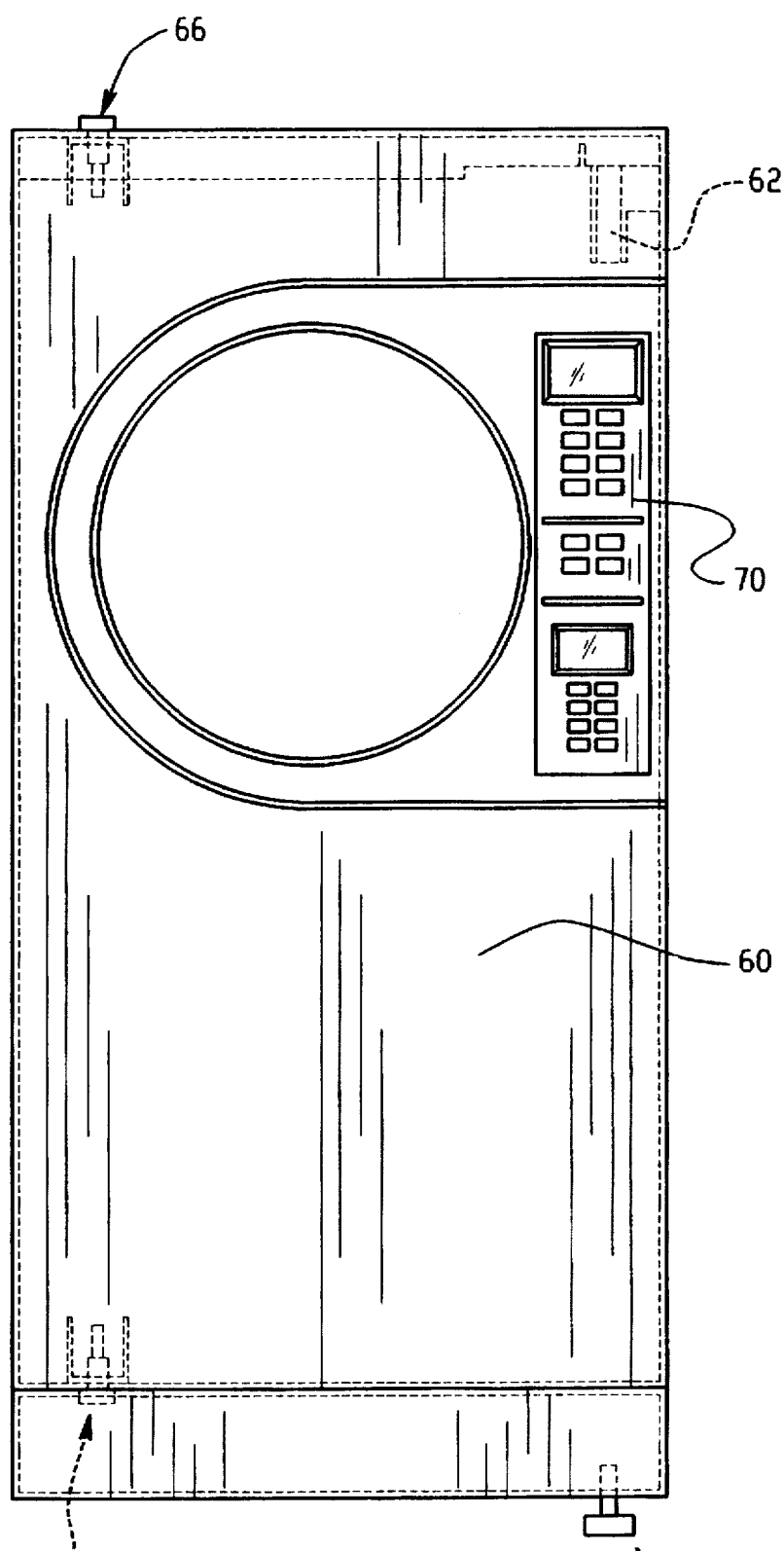
FIG. 7 is a front elevation view of the front panel of FIG. 1, partially in cross-section.

Referring now to the front panel 60, as most clearly depicted in FIG. 7, the panel is a molded plastic unit fixed to the sterilizer unit 10 via integral components including a hinge 62, a pivot pin 64, an upper lock 66 and a lower lock 68. The front panel 60 provides user controls 70 and access to the chamber interior. The controls are typically the control electronics in the form of buttons, read out displays and a paper print out. In the inventive design, the entire front panel is constructed of molded plastic and the control features are integral to the panel, resulting in low cost, low complexity of assembly and improved serviceability. More specifically, the control boards, digital display, touch pad and printer mounting surfaces are each provided with integral mounting surfaces to the front panel. Furthermore, the panel is constructed of a plastic material having insulate for properties to reduce the cost of adding insulation to a steel panel.

Referring now to FIGS. 5 and 6, the door cover assembly is depicted. Typical doors are constructed of steel with a sheet metal cover having an attached handle, the entire assembly therefore requiring full thermal insulation to maintain exterior cover temperatures at an acceptable level. As shown in FIGS. 5 and 6, the present inventive door is a steel door 72 having a molded cover 74 of heat resistant and insulating plastic secured thereover. The resilient plastic cover 74 is constructed to include a recessed handle mechanism 76, and includes laterally flexible side portions 78 which expand over the channels of the door 34 and are secured via a plurality of screws 80.

Thus, it is apparent there has been provided in accordance with the invention, a sterilization device that fully satisfies the objects, aims and advantages set forth above. While the invention is described in conjunction with specific embodiments thereof, it is evident that many alternatives, modifications, and variations will be apparent to those skilled in the art in light of the foregoing description. Accordingly, it is intended to embrace all such alternatives, modifications, and variations as well within the spirit and broad scope of the intended claims.

We claim:

1. A steam sterilization device comprised of a chamber including a vertically slidable sealable door, a flexible insulating plastic member covering said sealable door, a frame supporting said chamber and a track upon which said door is secured, an insulating front wall of molded plastic covering said frame, a recess for housing a control panel being formed integrally in said insulating front wall, a stop bracket secured to said track at an appropriate location below said door to limit travel of said door, said stop bracket having a generally rectangular shape including one bottom and four side walls with an open top, a cable interconnecting said door and at least one counterweight housed within a guide member, and a sensor secured within in a bore in said frame at a point suitable for indicating that said door is in a closed position.

2. The device of claim 1 wherein said front wall includes integral hinge and locking elements.

3. The device of claim 1 wherein said front panel includes an integral housing for a roll of printer paper.

4. The stop bracket of claim 1 wherein the upper surface of said bottom wall includes at least one elastomeric bumper.

5. The device of claim 1 wherein said counter weight is cylindrical.

6. The device of claim 1 wherein said guide member is tubular.

7. The device of claim 1 including casters that are height adjustable and rotationally lockable.

8. The device of claim 1 wherein said sensor is positioned within a bore in said frame said bore having a larger diameter portion and a narrower diameter portion adjacent said door.

9. The device of claim 1 including side panels secured to said frame.

10. The device of claim 1 wherein said track includes a coating of a low friction plastic.

11. The device of claim 1 wherein said plastic member includes an integrally formed handle.

12. A steam sterilization device comprised of a chamber rigidly secured to a frame, a selectively openable door attached to said chamber and a seal positioned between said door and said chamber to facilitate the creation of a high pressure environment within said chamber, a position sensor located to determine when said door is closed, said sensor secured within a bore in said frame, said bore having a first larger diameter end distant from said door and a second narrower diameter end proximate said door, and said sensor having a diameter narrower that of said first bore diameter end and wider than said second bore diameter end such that said sensor only partially penetrates through said frame.

13. The sterilization device of claim 12 wherein said bore and said sensor are cooperatively threaded.

14. A steam sterilization device including a pressurizable chamber having an open end, a slidable sealable door covering said open end and positioned on a pair of opposed tracks to allow vertical travel of said door between open and closed positions, an elongated member having a base portion generally positioned in the same vertical plane as said door and said base including four side walls and an open top and extending between said tracks, the elongated member acting as a stop for downward travel of said door and simultaneously acting as a catch basin for condensate from said open face of said chamber.

15. The device of claim 14 wherein said elongated member is generally rectangular shaped.

16. The device of claim 14 including resilient bumpers disposed within said elongated member.

17. The sterilization device of claim 14 wherein said base portion has a length substantially equal to a width of said door.

18. A steam sterilization device comprised of a chamber including a vertically slidable sealable door, a flexible insulating plastic member covering said sealable door, a frame supporting said chamber and a track upon which said door is secured, an insulating front wall of molded plastic covering said frame, a recess for housing a control panel being formed integrally in said insulating front wall, a stop bracket secured to said track at an appropriate location below said door to limit travel of said door, a cable interconnecting said door and at least one counterweight housed within a guide member, and a sensor secured within in a bore in said frame at a point suitable for indicating that said door is in a closed position wherein said bore has a larger diameter portion and a narrower diameter portion adjacent said door.

* * * * *